US006458834B2

(12) United States Patent
Glinski et al.

(10) Patent No.: US 6,458,834 B2
(45) Date of Patent: Oct. 1, 2002

(54) PENTACYCLIC TRITERPENES

(75) Inventors: Jan Glinski, New Fairfield, CT (US); Keith L. Branly, Brandon, FL (US)

(73) Assignee: Micro Flo Company, Memphis, TN (US)

( * ) Notice: Subject to any disclaimer, the term of this patent is extended or adjusted under 35 U.S.C. 154(b) by 0 days.

(21) Appl. No.: 09/822,478

(22) Filed: Apr. 2, 2001

Related U.S. Application Data

(62) Division of application No. 09/207,406, filed on Dec. 8, 1998.

(51) Int. Cl.[7] ........................ A01N 27/00; A01N 33/24; A01N 37/24; A01N 25/00; A01N 25/08; A01N 67/00

(52) U.S. Cl. ........................ 514/510; 514/766; 514/515; 514/784; 514/762; 514/640; 514/785; 514/169; 424/405; 424/407; 424/409

(58) Field of Search ................................ 514/510, 515, 514/784, 788, 762, 766, 785, 640; 424/405, 407, 409

(56) References Cited

U.S. PATENT DOCUMENTS

| | | | | |
|---|---|---|---|---|
| 4,942,184 A | 7/1990 | Haugwitz et al. | ........... | 514/449 |
| 5,679,828 A | 10/1997 | Lee et al. | ................... | 560/116 |
| 5,750,578 A | 5/1998 | Carlson et al. | ............. | 514/766 |
| 5,869,535 A | 2/1999 | Pezzuto et al. | ............. | 514/640 |
| 5,906,825 A | 5/1999 | Seabrook, Jr. et al. | ...... | 424/404 |

FOREIGN PATENT DOCUMENTS

| | | |
|---|---|---|
| GB | 2275194 | 8/1994 |
| RU | 1214679 | 2/1986 |

OTHER PUBLICATIONS

Food Microbiology, 1987, pp. 4, 311–315 (XP–001027623), "Antimicrobial Activity of Carnosol and Ursolic Acid: Two Anti–oxidant Constituents of *Rosmarinus officinalis l.*"; M.A. Collins and H. P. Charles; Academic Press Limited, 1987.

Fitoterapia, vol. LXIX, No. 1, 1998, pp. 43–46; "Chemotropism and Antimicrobial Activity of *Tamarindus indica*"; (XP–001027633) M. S. Ali, V. U. Ahmad, H.E.J. Research Institute of Chemistry, University of Karachi, Karachi—75270, Pakistan.

Plant Cell Reports, 1988, pp. 7:51–54; "Induction of Triterpene Biosynthesis by Elicitors in Suspension Cultures of Tabernaemontana Species"; (XP–001026845) R. van der Heijden, E. R. Verheij, J. Schripsema, A. Baerheim Svendsen, R. Verpoorte, and P. A. A. Harkes.

Advances in Experimental Medicine and Biology (Saponins Used in Traditional and Modern Medicine, Edited by Waller and Yamasaki, Plenum Press, New York, 1996); vol. 404, 1996, pp. 565–574, "Antifungal and Hemolytic Activity of Aerial Parts of Alfafa (Medicago) Species in Relation to Saponin Composition" (XP–001027666); G. R. Waller and M. Jurzysta.

Journal of Ethnopharmacology, 1994, pp. 115–119; "Antimicrobial Activity of *Visnea mocanera* Leaf Extracts"; M. Hernández–Pérez, R. E. López–Garcia, R. M. Rabanal V. Darias, A. Arias (XP–001026872).

Journal of Natural Products, vol. 44, No. 2, pp. 215–220; "Effects of Tetracyclic and Pentacyclic Triterpenoids On Growth of *Phytophthora Cactrum*", W. David Nes and Glenn W. Patterson, Department of Bolany, University of Maryland, College Park, MD (XP–001027647).

R. van der Heijden, et al., *Plant Cell Reports,* "Induction of Triterpene Biosynthesis by Elicitors in Suspension Cultures of Tabernamontana Species," pp. 7:51–54, 1988.

Robert van der Heuden, et al., *Phytochemistry,* "Regulation and Enzymology of Pentacyclic Triterpenoid Phytoalexin Biosynthesis in Cell Suspension Cultures of *Tabernaemontana divaricata*," vol. 28, No. 11, pp. 2981–2988, Mar. 1989.

Erich W. H. Hayek, et al., *Phytochemistry,* "A Bicentennial of Betulin," Review Article No. 26, Institute of Organic Chemistry, Technical University of Vienna, vol. 28, No. 9, pp. 2229–2242, Jan. 1989.

Jan A. Glinski, et al., "Inhibition of Elastase By Pentacyclic Triterpenes".

E.M. Varanda, et al., *Journal of Natural Products,* "Effect of Ursolic Acid from Epicuticular Waxes of *Jacaranda decurrens* on *Schizaphis graminum*," vol. 55, No. 6, pp. 800–803, Jun. 1992.

*Primary Examiner*—Sabiha Qazi
(74) *Attorney, Agent, or Firm*—Roylance, Abrams, Berdo & Goodman, L.L.P.

(57) ABSTRACT

The present invention relates to fuingicidally effective compositions containing at least one pentacyclic triterpene compound.

18 Claims, No Drawings

PENTACYCLIC TRITERPENES

This application is a divisional of copending U.S. application Ser. No. 09/207,406 filed on Dec. 8, 1998 the disclosure of which is herein incorporated by reference.

FIELD OF THE INVENTION

The invention relates to plant protection compositions including pentacyclic triterpenes and methods for use thereof.

BACKGROUND

Outer layers of plants such as leave cuticle, fruit peels, as well as bark protect the plant against abrasion, prevent water loss, and also protect against pathogenic microorganisms. The breaking through the plant cuticle is a prerequisite for a pathogen to be able to enter the plant's internal tissue.

The mechanism, by which plants naturally defend themselves against this early stage of pathogenesis has not been fully understood. The initial process of fungal propagules attaching to a host plant is essential to the successful establishment of pathogenesis. The established facts that aerial fungal pathogens bind strongly to very hydrophobic surfaces suggests that hydrophobic forces are involved in the attachment processes.

The attachment of aerial fungal pathogens involves an active process of secretion of extracellular mucilages or adhesives, which may start within minutes after contact with the host. Other reported components in the adhesive secretions include enzymes, among them esterases and cutinases. The erosion of cuticular waxes adjacent to and underlying the conidium may became observable within 20 min of liquid release. The growth of the appressorial germ tube appears to be limited to the zone of deposition of the liquid film.

Some studies have suggested that preparation of the infection court involves active dissolution of the host cuticle by foliar pathogen. It is also believed that this dissolution is the purpose of these enzymes. Nicholson, R. L., and L. In: *The Fungal Spore and Disease Initiation in Plants and Animals*., Eds. Cole, G. T., and Hoch, H. C.,1991 Plenum Press, New York, 3–23. Thus, the cuticle has to be penetrated by the attacking pathogen before the sequential steps of disease development occur. Some fungal spores help themselves with mechanical force exerted by the infection structure in addition to the enzymatic degradation. (Köller, W. in: *The Fungal Spore and Disease Initiation in Plants and Animals*., Eds. Cole, G. T., and Hoch, H. C., 1991 Plenum Press, New York, 219–246.

Pentacyclic triterpenes (PT) are among the most common plant secondary metabolites, but their function in plants have not been understood. They are usually concentrated in the outermost layers such as plant cuticle, fruit peel and bark. In some cases, these layers contain very high concentration of pentacyclic triterpenes. For example, an apple peel contains about 0.1 grams of ursolic acid per fruit, and the outer bark of white birch species contains up to 40% w/w of betulin. The amount of betulin obtainable from the birch bark waste in the wood-working industry in Finland is estimated at about 150,000 tons per annum. At present, waste bark is used as a low value fuel for energy production. Jääskeläinen, P. (1981) Pap. Puu 63, 599–603.

Literature supplies numerous examples of enzymes that can be inhibited by PT, indicating the ability of PT to act broadly in a non-specific mode on multiple targets. See for example, (a.) Büchler et al. (1991) *Biochem. Biophys. Acta* 1075, 206–212, Inhibition of rat renal 11β-hydroxysteroid dehydrogenase by steroidal compounds and triterpenoids; structure/function relationship; (b.) Koch et al. (1994) *Phytother. Res.* 8, 109–111, In vitro inhibition of adenosine deaminase by a group of steroid and triterpenoid compounds.; (c.) Najid et al. (1992) *FEBS* 299, 213–217, Characterization of ursolic acid as a lipoxygenase and cyclooxygenase inhibitor using macrophages, platelets and differentiated HL60 leukemic cells.; (d.) Pengsuparp et al. (1994) *J. Nat. Prod.* 57, 415–418, Pentacyclic triterpenes derived from *Maprounea africana* are potent inhibitors of HIV-1 reverse transcriptase.; (e.) Simon et al. (1992) *Biochem. Biophys. Acta* 1125, 68–72, Inhibition of lipoxygenase activity and HL60 leukemic cell proliferation by ursolic acid isolated from heather flowers (*Calluna vulgaris*).; (f.) Ying et al. (1991) *Biochem. J.* 277, 521–526 Inhibition of human leucocyte elastase by ursolic acid. Evidence for a binding site for pentacyclic triterpenes. The disclosures of each of these references is herein incorporated by reference.

In plant tissue cultures, stress induced by inactivated fungi or fungal enzymes has been used to enhance production of biologically active secondary metabolites. In several instances it has been reported that this fungal elicitation led to overproduction of pentacyclic triterpenes instead of some other expected metabolites. Suitable example is given by Van der Heijden et al., (1988) *Plant Cell Rep.* 7, 51–54, where tissue cultures of Tabernaemontana spp., normally producing indole alkaloids, were subjected to stress induced by either fungi, bacteria, or enzyme cellulase or pectinase. When stressed, however, the culture produced up to 3.3 times the normal rate of the ursane-type pentacyclic triterpenes (2% of dry mass) but no increase in the production of indole alkaloids occurred.

Other experiments with *Tabernaemontana divaricata* treated with *Candida albicans* elicitor led to production of a series of pentacyclic triterpenes of the ursane and oleane types, and was accompanied by inhibition of both growth and indole alkaloid accumulation (Van der Heijden et al., (1989) *Phytochemistry* 28, 2981–1988).

Also, the tissue culture of *Tripterygium wilfordii*, normally a source of potent cytotoxic diterpenes, stressed by fungal Botrytis elicitor dramatically enhanced production of oleane-type pentacyclic triterpenes but not the diterpenes, prompting a conclusion that only triterpenes are inducible anti-microbial phytoalexins. Kutney, et al., (1993) Anti-inflammatory oleane triterpenes from *Tripterygium wilfordii* cell suspension cultures by fungal elicitation. *Plant Cell Rep.* 12, 356–359.

The conventional treatments for leafy and grassy plants that have been attacked by fungi and bacteria are usually exercised after an outbreak occurs. The affected plants are then treated with one or more of the commercial synthetic contact antimicrobial sprays at application rates that do not pose phytotoxicity concerns. Effective treatment rates must be balanced against the risks of harming the treated plant with chemicals that are structurally unrelated to those in the plant physiology. It would be desirable to have a protective agent that is effective against microbial pathogens which would also work in a manner analogous to the plant's natural defense mechanisms to reduce the risk of phytotoxicity. One of the problems associated with treating hydrophobic leaf surfaces is an effective application of the material. Current spraying techniques result in a portion of the sprayed material falling to the ground directly or after being washed off from rain occurring shortly after application. Either event increases concerns for environmental contamination.

Protective agents that are applied by spraying should remain on the plant surface for a time sufficient to serve their intended function. Stability against ultraviolet and visible light is, therefore, a concern for foliar treatments. It would be desirable to develop fungicides for foliar application that resist degradation by exposure to ultraviolet as well as visible light.

Moreover, invading organisms have been known to evade the effects of a treatment agent by mutation and propagation of resistant strains. Such developed resistance is economically detrimental because it forces the discovery of new treatments. It would be helpful to provide plant anti-infective agents which cannot be evaded by mutating pathogens.

SUMMARY OF THE INVENTION

It is an object of the invention to provide a composition and process for use thereof for protecting plant surfaces against microbial pathogens with ingredients that are compatible with natural plant defense mechanisms.

It is another object of the invention to provide a composition and method of use that poses little risk to the environment, humans, or beneficial insects.

It is another object of the invention to provide plant anti-infective agents, which cannot be evaded by developing resistance by mutating pathogens.

It is yet another object of the invention to provide a composition having good resistance to degradation by ultraviolet exposure, long storage times, and good inherent sticking ability to plant surfaces.

In accordance with these and other objects of the invention, which will become apparent from the description herein, a composition according to the invention comprises: a pentacyclic triterpene or a mixture of pentacyclic triterpenes, including some plant extracts that are particularly rich in pentacyclic triterpenes, having as main components compounds described by any of formulas I, II, or III.

A method according to the invention comprises applying to plant surfaces an effective amount of a composition comprising a pentacyclic triterpene or a mixture of pentacyclic triterpenes exhibiting any of formulas I, II or III.

Formulas I, II, and III are:

I

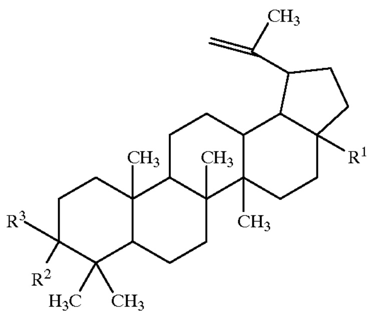

-continued

II

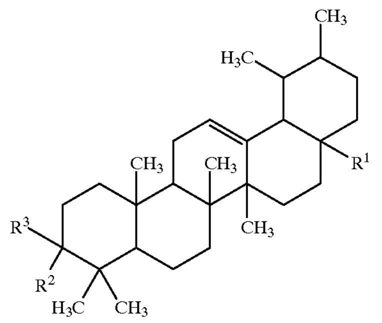

III

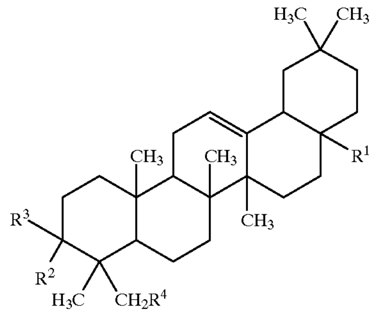

wherein:

$R^1$=Me, $CH_2OH$, $CH_2OY^1$, $CH_2O$—X—OH, $CH_2O$—X—$OY^1$, $CH_2O$—X—$Y^2$, $CH_2O$—X—$Y^3$, $CH_2NHY^1$, $CH_2NY^1{}_2$,$CH_2Y^3$, $CH_2NH$—X—OH, $CH_2NH$—X—$Y^2$, $CH_2NH$—X—$Y^3$, $CH_2NH$—X—$OY^1$, $CH_2OC(O)$—$OY^1$, $CH_2O$—X—$OY^1$, $CO_2Y^1$, $COY^3$, $COY^2$, CHO, CH═$N(CH_2)_m(O(CH_2)_m)_nR^4$, or CH═$N(CH_2)_m(O(CH_2)_m)_nY^2$;

$R^2$, $R^3$=H, OH, $OY^1$, O—X—OH, O—X—$OY^1$, O—X—$Y^2$, $Y^3$, $NHY^1$, $NY^1{}_2$, $Y^3$, NH—X—OH, NH—X—$Y^2$, NH—X—$Y^3$, NH—X—$OY^1$, $NY^1$—X—OH, $NY^1$—X—$Y^2$, $NY^1$—X—$Y^3$, or $NY^1$—X—$OY^1$; provided that one of $R^2$ and $R^3$ is H or that $R^2$ and $R^3$ together denote carbonyl oxygen;

$R^4$=H, OH, $OY^1$, or $Y^3$;

$Y^1$=H, alkyl of 1–30 carbon atoms, straight chain or branched, cycloalkyl of 3–30 carbon atoms, alkanyl of 3–30 carbon atoms, oxyalkyl of 4–30 carbon atoms, phenylalkyl of 7–30 carbon atoms, or phenoxyalkyl of 7–30 carbon atoms;

$Y^2$=$NH_2$, $NHY^1$, or $NY^1{}_2$;

$Y^3$=—$(O(CH_2)_m)_nR^4$ or —$(O(CH_2)_m)_nY^2$, where m=2–4 and n=1–230;

X=—$OC(CH_2)_pCO$— where p=1–22.

The present invention provides a composition and method of use that are particularly effective in preventing outbreaks of airborne fungal and bacterial diseases on treated plant surfaces. The pentacyclic triterpenes of the composition are applied to form a film over the plant surface. The film of material prevents the prerequisite attachment of aerial fungal pathogen and penetration of the plant cuticle. In addition, the compounds are not phytotoxic and are compatible with natural plant defenses

DETAILED DESCRIPTION

The present invention relates to compositions containing and methods of using pentacyclic triterpenes having the following formulas I, II, or III:

I

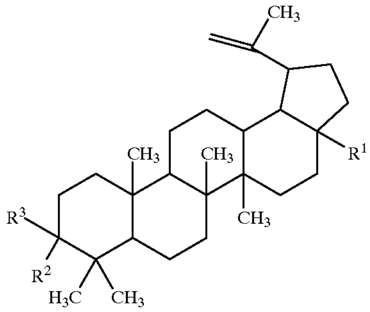

II

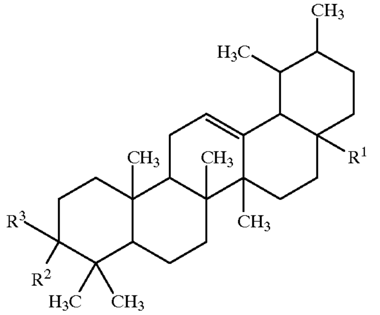

III

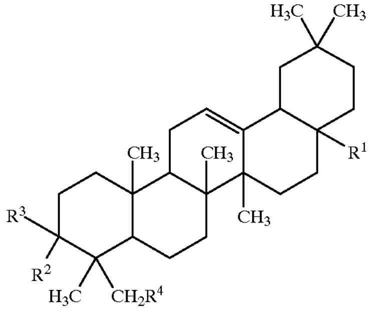

wherein:

$R^1$=Me, $CH_2OH$, $CH_2OY^1$, $CH_2O$—X—OH, $CH_2O$—X—$OY^1$, $CH_2O$—X—$Y^2$, $CH_2O$—X—$Y^3$, $CH_2NHY^1$, $CH_2NY^1{}_2$,$CH_2Y^3$, $CH_2NH$—X—OH, $CH_2NH$—X—$Y^2$, $CH_2NH$—X—$Y^3$, $CH_2NH$—X—$OY^1$, $CH_2OC(O)$—$OY^1$, $CH_2O$—X—$OY^1$, $CO_2Y^1$, $COY^3$, $COY^2$, CHO, CH═$N(CH_2)_m(O(CH_2)_m)_nR^4$, or CH═$N(CH_2)_m(O(CH_2)_m)_nY^2$;

$R^2$, $R^3$=H, OH, $OY^1$, O—X—OH, O—X—$OY^1$, O—X—$Y^2$, $Y^3$, $NHY^1$, $NY^1{}_2$, $Y^3$, NH—X—OH, NH—X—$Y^2$, NH—X—$Y^3$, NH—X—$OY^1$, $NY^1$—X—OH, $NY^1$—X—$Y^2$, $NY^1$—X—$Y^3$, or $NY^1$—X—$OY^1$; provided that one of $R^2$ and $R^3$ is H or that $R^2$ and $R^3$ together denote carbonyl oxygen;

$R^4$=H, OH, $OY^1$, or $Y^3$;

$Y^1$=H, alkyl of 1–30 carbon atoms, straight chain or branched, cycloalkyl of 3–30 carbon atoms, alkanyl of 3–30 carbon atoms, oxyalkyl of 4–30 carbon atoms, phenylalkyl of 7–30 carbon atoms, or phenoxyalkyl of 7–30 carbon atoms;

$Y^2$=$NH_2$, $NHY^1$, or $NY^1{}_2$;

$Y^3$=—$(O(CH_2)_m)_nR^4$ or —$(O(CH_2)_m)_nY^2$, where m=2–4 and n=1–230;

X=—$OC(CH_2)_pCO$— where p=1–22.

The preferred pentacyclic triterpenes include betulin, betulinic acid, ursolic acid, oleanolic acid, betulin mono- and di-succinate or glutarate, as well as polyethylene glycol derivatives of thereof.

Particularly useful are those pentacyclic triterpenes exhibiting an $IC_{50}$ value against human leucocyte elastase at concentration less than about 15 micromolar (μM), more preferably an $IC_{50}$ value of less than about 10, and most preferably an $IC_{50}$ value at less than about 8 micromolar. The $IC_{50}$ value represents the concentration of an inhibitor, which can be expressed in micromoles per liter, at which activity of an enzyme is reduced by 50%. Thus, lower $IC_{50}$ values suggest higher levels of enzyme inhibitory activity.

The pentacyclic triterpenes of the invention are the same as, derived from, synthesized, or otherwise related to those found naturally in the outer surfaces of plants: leaves, fruits, bark, and are subjected to pathogenesis involving enzymatic degradation of cuticle. For the present invention, the pentacyclic triterpenes or their derivatives are applied to the exposed outer plant surfaces in conjunction with a suitable carrier such as water, an aqueous film-forming solution, detergents, emulsion forming additives, suitable polymers to enhance physical properties of the sprayed layer.

Pentacyclic triterpenes can be obtained by extracting the pentacyclic triterpene-containing plant tissues with one or more organic solvents suitable for the triterpenes. Preferred plant tissue sources for PT include bark from white birch trees, apple peels, and the leaves of plants belonging to Vaccinium and Myristica spp. Useful solvents for the extraction include ethyl acetate, acetone, methyl ethyl ketone, ethanol, propanol, isopropanol, methanol, methylene chloride, chloroform, or their mixtures.

The pentacyclic triterpenes or their polyethylene glycol derivatives of the invention should be formed in a non-crystalline state into a well mixed colloidal suspension for application as a uniform coating on the treated plant surfaces. The uniform coating helps to ensure that plant surfaces are well protected against pathogens with the exception of under surfaces or secluded regions unable to be reached by conventional spraying equipment for liquid formulations.

The pentacyclic triterpene compounds of the invention are, however, crystalline solids of hydrophobic character. The solids can be dissolved in a number of solvents suitable for agricultural use. If desired, the solutions or colloidal concentrates of pentacyclic triterpenes can be prepared for shipping and storing. This concentrate can then be further diluted for use by a formulator or applicator.

A preferred solvent for pentacyclic triterpene solids contains about 1–25 wt % acetone, about 0–10 wt % dimethylsulfoxide (DMSO), 0–35% polyethyleneglycol ester of an aliphatic acid, and about 0–25 wt % of a surfactant such as commercially available detergents like Tween 80™ or Palmolive™ dishwashing detergent. Generally, this solvent mixture may carry a concentration of a PT being 1500–4000%, by weight, of that needed for application to the plants.

The concentrate can be further diluted with 100–4000%, preferably 300–1000% by weight of water to make a sprayable composition according to the invention. Particularly useful concentrations are within the range from about 7–30 grams per gallon of water. Adequate mixing requires only low to moderate shearing to ensure adequate mixing of the concentrate during dilution. For example, metering the concentrate into a reservoir attached to a venturi mixer would provide adequate shear to completely mix the concentrate with additional water.

Pentacyclic triterpenes or their polyethylene glycol derivatives according to the invention are applied at a rate sufficient to prevent pathogenic infections. The inhibitory properties of PT are utilized by the plants to inactivate the enzymes excreted by the fungal spore in order to degrade the plant cuticle. Suitable application rates for effective protection include rates within the range from about 0.1–1000 kg/h. Preferably, the application rate is within the range from about 0.1–100 kg/h. The specific application rate that is best for a particular type of plant in a particular region is readily determined by the application of the ordinary skill in the art. The application should, however, be designed to fall on and cover the exposed leaf surfaces of the plants being treated such as it occurs with conventional foliar treatments using conventional foliar spraying equipment.

If desired, the PT or their polyethylene glycol derivatives may be applied in conjunction with one or more inert or active ingredients. Exemplary materials include dyes, additives affecting stability of the concentrate and additives affecting physical properties of the sprayed layer, foliar fertilizers, fungicides, and insecticides.

Virtually any plant that may get infected through the waxy cuticle layer can be beneficially treated with compositions according to the present invention. Commercial plants that would benefit include grain grasses (e.g., rye, wheat, and barley), tomato, bean, pepper, wheat, and peanut plants.

Grain grasses may benefit in particular from the present invention. These plants do not generally produce sufficient levels of pentacyclic triterpenes, if at all, to inhibit enzymatic attacks by invading microorganisms. Natural pathogens of these plants are generally not adapted to produce sufficient amounts of enzymes to overcome the inhibiting effects of the externally applied pentacyclic triterpene compounds.

Plants susceptible to small insect (e.g., aphids) infestation also benefit from treatment according to the invention. Ursolic acid showed toxicity and feeding deterrent effects towards the mites and their survival. The mites' reproductive indexes decreased in direct proportion to ursolic acid content in the diet, and in addition, ingestion time on diet containing ursolic acid was reduced about 30% (Varanda et al., 1992). These observations imply a possibility that the insect's digestive enzymes were compromised by ursolic acid.

The mode of inhibition of enzymes by PT is non-specific and is based primarily on hydrophobic interaction with an enzyme's hydrophobic domain. This property suggests that the likelihood for developing microbial pathogen resistance through mutation is remote. Pathogens had to deal with the presence of PT in the plant cuticle for as long as the plants existed and it could be assumed that microbial resistance to the PT has been already optimized. The PT based formulations for plant protection should be advantageous against the pathogenic microorganisms that use enzymes to break through the cuticle, such as fungi, bacteria, nematodes and viruses. These formulations should be also advantageous against small insects, acting inhibitory on their digestive enzymes. By covering the leafy surface with a film containing pentacyclic triterpenes, the passive defensive properties of the cuticle are enhanced, which decreases or entirely prevents successful pathogenic penetration.

The following examples are included to assist in an understanding of the invention and are not intended to limit the scope of the attached claims.

EXAMPLES

Commercially available compounds were acquired either from Extrasyntheses (France), Aldrich, Sigma or ICN Pharmaceuticals. Melting points were obtained using a Reichert Thermovar melting point apparatus and are corrected. Hnmr spectra were acquired in $C_5D_5N$ with TMS as an internal standard (δ=0.0 ppm) using a Bruker WM-250 or 270 NMR spectrometer. Mass spectra were acquired using a Finnigan 4023 EI/CI GCMS mass spectrometer with Super-INCOS software and direct insertion probe.

Examples 1a and 1b

Synthesis of 28-hemisuccinylbetulin and 3,28-Di-hemisuccinylbetulin.

Example 1a

A reaction mixture is prepared by dissolving imidazole (4 eq) and succinic anhydride (1.08 eq) in N-methylpyrrolidone. The volume of the solvent is about 4.5 times the weight of betulin. When the two reagents are dissolved, betulin (1 eq) is added. The reaction mixture is left at room temperature with occasional shaking. After approximately 48 hrs, about 92–95% of the betulin has been converted into 28-hemisuccinilbetulin, with 2–4% as unconverted betulin and diacylbetulin.

The 28-hemisuccinilbetulin is purified by pouring the reaction mixture into a 20× volume of water with slow stirring. The water is decanted from the solid residue and the washing is repeated with several new portions of water. The solid is separated, dried and dissolved in a mixture of chloroform and isopropanol. The chloroform is removed by evaporation enabling 28-hemisuccinylbetulin to form and crystallize. The 28-hemisuccinylbetulin crystals are white with a melting point of 242–244° C.

Calculations for $C_{34}H_{54}O_5$, C, 75.22%, H, 10.03; found C, 75.0, H, 9.91. The $^1$Hnmr (DMSO-$d_6$) gave peaks at: 4.86 and 4.72 (1H, s, each, $CH_2$=C), 4.57 and 4.14 (AB pattern, J=12 Hz, $OCH_2O$), 3.44 (1H, t, J=8.6 Hz), 2.95 (4H, s, $CHOCH_2CH_2CO$), 1.71, 1.22, 1.02, 0.98, 0.98, 0.84 (s, each, Me); eims (m/z, rel. int.): 524 (20, [M−$H_2O$]+), 424 (15), 411 (27), 207 (38), 203 (41), 189 (100), 135 (70), 119 (61), 107 (62), 95 (81), 81 (79), 55(90%); cims: 543 (11, M+), 525(64, [MH−$H_2O$]+), 425(80), 407 (100), 217 (91), 203 (90), 191 (48), and 189 (52%).

Example 1b

Betulin, 443 mg (1 mmole), imidazole, 227 mg (4 mmoles), succinyl anhydride, 400 mg (4 mmoles) and 0.6 ml of methylpyrrolidone were combined in a vial. The reaction mixture was maintained at 70° C. for 20 hrs. The reaction mixture was then added dropwise to 100 ml of water and stirred for half an hour. The resulting precipitate was filtered off, re-suspended and agitated in another portion of water in order to remove the remaining reactants. This procedure was repeated several times until no more of the reactants were washed out. The solid was collected, dried and dissolved in acetone. The acetone solution was filtered and evaporated to give 470 mg of 3,28-dihemisuccinylbetulin.

Calculated for: $C_{38}H_{58}O_8\cdot\frac{1}{4}H_2O$, MW 642.84; C, 70.5%, H, 9.1%; found C 70.43%, H 9.15%. 1H NMR: 4.70 and 4.61 (1H, s, each, =CH2), 4.52 (1H, dd, $J_1$=5.4 Hz, $J_2$=10.0 Hz), 4.33 and 3.90 (1H, d, each, AB pattern, J=11.1 Hz, $OCH_2$), 2.63 –2.71 (8H, m, succinyl chain), 1.70, 1.05, 0.99, 0.87, 0.86, and 0.85 (Me, s, each). MALDI-TOF-MS gave m/z 665 (M+$Na^+$) and also m/z 542 and 525.

Example 2

Synthesis of Acetylbetulinic Acid.

Betulinic acid, 100 mg (0.22 mmoles) was added to a solution containing 4 mg of 4-dimethylaminopyridine (DMAP) and 0.5 ml of $(CH_3CO)_2O$ in 5 ml of $CH_2Cl_2$. After 2 hrs $CH_2Cl_2$ was removed in vacuo, and the remaining residue stirred with 25 ml of water. During the stirring enough of $K_2CO_3$ was added to decompose an excess of acetic anhydride, after which the reaction mixture was extracted with 25 ml of $CH_2Cl_2$. The extract was evaporated to dryness and the resulting solid crystallized from MeOH to give 104 mg of acetylbetulinic acid as white crystals, m.p. 285° C.

Calculations for $C_{32}H_{50}O_4$, C, 77.06, H, 10.10; found C, 77.02, H, 10.08%. The $^1$Hnmr DMSO-$d_6$) gave peaks at: 4.93 and 4.76 (1H, s, each, $CH_2$=C), 4.67 (1H, dd, C3—H, J=5.0, 10.0 Hz), 2.05 (s, $CH_3CO$), 1.78, 1.06, 1.00, 0.87, 0.84 and 0.73 (each, s, $CH_3$); eims (m/z, relative intensity): 499 (1, MH+), 452 (2), 438 (38), 395 (26), 189 (40), 43 (100%); cims (m/z, rel. intensity): 499 (37, MH+), 440 (27), 439 (100), 437 (18), 393 (20), 203 (15), 191 (24%).

Example 3

Synthesis of 3-methanesulfonylbetulinic Acid.

Betulinic acid, 100 mg (0.22 mM) was dissolved in 5 ml of pyridine and treated with 100 mg (0.88 mmoles) of $CH_3SO_2Cl$. After 16 hrs, the pyridine was removed in vacuo and the resulting residue suspended in 10 ml of water. Excess of $MeSO_2Cl$ was decomposed with an aqueous $NaHCO_3$ solution, and the reaction mixture extracted with 10 ml of $CH_2Cl_2$. Evaporation of the solvent gave a crude product containing 3-methanesulfonylbetulinic acid, which was purified by column chromatography over 3 g of silica gel using $CH_2Cl_2$ with 0 to 5% gradient of MeOH. The chromatography afforded 3-methanesulfonylbetulinic acid, which on crystallization from MeOH gave 62 mg of white crystals, m.p. 210–212° C.

Calculations for $C_{31}H_{50}O_5S$: C, 69.62, H, 9.42, S, 6.00; found C, 69.78, H, 9.46, S, 5.90%. $^1$Hnmr (DMSO-$d_6$): 4.95 and 4.78 (1H, each, s, $CH_2$=C), 4.50 (1H, dd, J 4.6, 11.8 Hz), 3.30 (3H, s, $CH_3SO_2$), 1.79, 1.07, 1.06, 1.00, 0.82, 0.72 (each, s, $CH_3$); eims (m/z, relative intensity): 438 (9), 423 (11), 395 (72), 259 (12), 161 (26), 135 (62), 121 (100), 107 (60), 93 (61), 79 (54%); cims (m/z, rel. intensity): 535 (11, MH+), 439 (91), 423 (25), 395 (52), 249 (12), 203 (28), 191 (34), 97 (100%).

Example 4

Synthesis of the Methyl Ester of 3-methanesulfonylbetulinic Acid.

Betulinic acid methyl ester, 500 mg (1.06 mmoles), and 320 mg (3.3 mmoles) of $Me_3N$ were dissolved in 10 ml of $CH_2Cl_2$. The solution was cooled in an ice-bath and treated with 190 mg (1.7 mmoles) of $MeSO_2Cl$. The reaction mixture was allowed then to warm up to room temperature and left overnight. Evaporation of the solvent in vacuo left a residue, which was dissolved in 10 ml of $Et_2O$ and washed 3 times with 5 ml $H_2O$. The etheral layer was dried over $MgSO_4$, filtered, and evaporated to give 582 mg of the methyl ester of 3-methanesulfonylbetulinic acid. Recrystallization from EtOH gave crystals with a melting point of 190° C.

Calculation for $C_{32}H_{52}O_5S$: C, 70.03, H, 9.55, S, 5.84; found C, 69.85, H, 9.50, S, 5.65%. $^1$Hnmr (DMSO-$d_6$): 4.89 and 4.73 (1H, each, $CH_2$=C), 4.47 (1H, dd, C3—H, J=2.5, 12.5 Hz), 3.70 (s, $OCH_3$), 3.29 (s, $CH_3SO_2$), 1.72, 1.04, 0.99, 0.92, 0.81, 0.72 (s, each, $CH_3$); eims (m/z, relative intensity): 452 (9), 409 (14), 341 (8), 273 (15), 255 (12), 189 (100), 175 (47), 121 (72), 107 (72), 93 (76), 79 (85%); cims (m/z, rel. intensity): 549 (16%, MH+), 453 (100), 393 (19), 203 (13), 189 (12), 97 (80%).

Examples 5–24

Elastase Inhibition

Studies, performed with human leucocyte elastase (HLE) indicated that many common naturally occurring PTs with lupane, oleane, and ursane skeletons inhibit HLE at low micromolar concentrations. Several derivatives of these PTs were prepared using synthetic methodology to explore structure-activity relationship and on testing they also inhibited HLE. The values of inhibitory constants, $IC_{50}$'s obtained from HLE inhibition, for the tested compounds, are given in Table 1.

Stock solutions were mixed to yield a reaction mixture consisting of 0.5 mM MeO-Suc-Ala-Ala-Pro-Val-pNA (Sigma) and 0.7 μmg/ml human leucocyte elastase (Elastin Products) in 0.1 M Tris, 0.5 M NaCl and 3% DMSO (v/v) at a pH of 7.5. Test compounds were solubilized in DMSO. Equal volumes of enzyme and inhibitor were mixed and allowed to incubate for 15 minutes at room temperature. The reaction was started by the addition of a third equal volume containing substrate. Reactions were carried out in microliter plates. Appearance of p-nitroaniline was monitored at 405 nm in a Dynatech microelisa Reader M600. Initial rates in the presence and absence of test compound were compared to determine $IC_{50}$ values which are reported in Table 1.

TABLE 1

| Ex. | Compound Name | $IC_{50}$ (μM) |
|---|---|---|
| 5 | Lupeol | 8.4 |
| 6 | Lupeol acetate | 14.9 |
| 7 | Betulin | 5.0 |
| 8 | 28-Succinylbetulin | 6.3 |
| 9 | Betulinic acid | 3.3 |
| 10 | Methyl ester of betulinic acid | 5.7 |
| 11 | Acetylbetulinic acid | 7.0 |
| 12 | 3-Ketobetulinic acid | 11.0 |
| 13 | Methanesulfonylbetulinic acid | 11.2 |
| 14 | Methyl ester of 3-methanesulfonylbetulinic acid | 7.3 |
| 15 | β-Amyrin | 5.4 |
| 16 | Uvaol | 4.5 |
| 17 | Ursolic acid | 7.7 |
| 18 | Ursolic acid, Me ester | 4.9 |
| 19 | α-Amyrin | 21.1 |
| 20 | Oleanolic acid | 18.7 |
| 21 | Oleanolic acid, Me ester | 8.5 |
| 22 | Echinocystic acid | 21.1 |
| 23 | Hederagenin | 16.8 |
| 24 | Caulophyllogenin | 0% @ 21° |

Further experiments, carried out with ursolic acid and oleanolic acid, indicated that these compounds can inhibit also other enzymes, such as plasmin and urokinase. The values of inhibition, measured at 22 μM in the plasmin assay were 43% for ursolic acid and 25% for oleanolic acid, while in the urokinase assay were 83% for ursolic acid and 40% for oleanolic acid. For betulinic acid, in the following assays, $IC_{50}$ values were determined to be: thrombin 2.3, trypsin 8.5, plasmin 6.2, and urokinase 5.0 μM. The apparent lack of specificity within the tested enzymes and an observation that the inhibition ceases in the presence of 0.1% of albumin suggested that the inhibition results from a non-specific binding to proteins. Thus, PTs appear to bind non-covalently to hydrophobic domains of enzymes and either block an access to the enzyme active site or cause conformational change, both resulting in the enzyme's inability to perform its function.

The most potent inhibitors of the investigated group of PTs contain one to three oxygenated substituents, such as hydroxy or carboxy groups. These moieties contribute to the overall inhibitory effect of the compounds.

Examples 25

Fungicidal Activity

Tomato, bean, pepper, wheat, and peanut plants are grown for one to three weeks (depending upon species) in the greenhouse. Two pots, which represent two replicates, of each plant species are placed into a flat such that each flat contains all the plants to be sprayed by one compound. The plants in each flat are sprayed to runoff with the desired spraying solution or with fungicide standard. As a control, check plants are sprayed with water. The plants are allowed to air-dry two to three hours. After the plants are dry, they are sorted and grouped by plant species.

Table 2 identifies the compositions of examples 25–28 that were tested for their ability to protect hydrophobic plant surfaces:

TABLE 2

| Example | Material |
|---|---|
| 25 | Control vehicle containing acetone 18 ml, dimethylsulfoxide 4 ml, and Palmolive ™ detergent 200 mg. Tested as 3% aqueous concentration. |
| 26 | 40 mg betulin dissolved in 1.5 ml of vehicle and added to 98.5 ml of water. |
| 27 | 80 mg betulin, 3.0 ml of vehicle, and 97 ml of water. |
| 28 | 40 mg of ursolic acid, 2.0 ml of vehicle, and 98 ml of water. |

The plant pathogenic fungi *Phytophthora infestans* (Pi), *Alternaria solani* (As), *Botrytis cinerea* (Bc), and *Cercospora arachidicola* (Ca) were grown in the laboratory on appropriate media. Inoculum from each fungus was harvested and concentrations adjusted to predetermined levels. The obligate plant pathogenic fungi (*Erysiphe graminis* f.sp. *tritici, Puccinia recondita* f.sp. *tritici*) are harvested from their hosts in the greenhouse and concentration are adjusted to predetermined levels.

The plants previously treated with test compounds are sprayed with fungal inoculum then placed in humidity chambers for a period of time which is found to be optimum for development of each disease. After incubation, the plants are moved to the greenhouse, symptoms allowed to develop, and the plants evaluated for disease intensity. Table 3 reports the percent disease control as the average of two replicates.

TABLE 3

| | Disease (% control) | | | | | | |
|---|---|---|---|---|---|---|---|
| Example | Pi | Pv | As | Bc | Sn | Pr | Eg |
| 25 | 8 | phytotoxic | 5 | 12 | 0 | 0 | 0 |
| 26 | 0 | 0 | 17 | 3 | 0 | 0 | 0 |
| 27 | 40 | 0 | 3 | 7 | 0 | 0 | 0 |
| 28 | 65 | phytotoxic | 8 | 33 | 0 | 0 | 0 |
| 29 | 33 | 0 | 12 | 12 | 0 | 0 | 0 |

Pi. *Phyophthora infestans*; Late blight tomato
Pv: *Plasmopara viticola*; Grape mildew
As: *Alternaria solani*; Early blight tomato
Bc: *Botrytis cinerea*; Gray mold
Sn: *Septoria nodorum*
Pr: *Puccinia recondita*; Wheat leaf rust
Eh: *Erysiphe graminis*; Powdery mildew wheat Following review of the control achieved by examples 25–29, the concentration of pentacyclic triterpene and carrier vehicle were changed. Table 4 identifies the compositions of examples 30–35, and Table 5 shows the percent control of plant diseases following a protective application of materials in examples 30–35. The results in table 5 are the mean of three replicates.

TABLE 4

| Example | Composition |
|---|---|
| 30 | Carrier vehicle containing 0.35% solution of Tween 80 ™ in water. |
| 31 | 200 mg betulin in 100 ml of carrier. |
| 32 | 400 mg betulin in 100 ml of carrier. |
| 33 | 800 mg betulin in 100 ml of carrier. |
| 34 | 400 mg ursolic acid in 100 ml of carrier. |

TABLE 5

| | Disease (% control) | | | | | | | | |
|---|---|---|---|---|---|---|---|---|---|
| Ex. | Pi | Pv | As | Bc | Sn | Pr | Eg | Sm-p | Sm-t |
| 30 | 7 | 0 | 43 | 94 | 0 | 0 | 0 | 50 | 30 |
| 31 | 10 | 0 | 47 | 100 | 0 | 0 | 0 | 60 | 20 |
| 32 | 7 | 37 | 53 | 82 | 0 | 0 | 0 | 65 | 30 |
| 33 | 60 | 0 | 63 | 97 | 0 | 0 | 0 | 50 | 30 |
| 34 | 0 | 0 | 0 | 60 | 0 | 0 | 0 | 40 | 60 |

Pi: *Phytophthora infestans*; Late blight tomato
Pv: *Plasmorara viticola*; Grape mildew
As: *Alternaria solani*; Early blight tomato
Bc: *Botrytis cinerea*; Gray mold
Sn: *Septoria nodorum*
Pr: *Puccinia recondita*; Wheat leaf rust
Eh: *Erysiphe graminis*; Powdery mildew wheat
Sm-p: *Sclerotinia minor*; Sclerotinia blight (on peanut)
Sm-t: *Sclerotinia minor*; Sclerotinia blight (on tomato)

As seen from Table 5, an increase in the amount of applied betulin generally increased control in susceptible fungus.

What is claimed is:

1. A composition useful for inhibiting enzyme-based attacks on plant surfaces comprising:

a) a carrier selected from the group consisting of aqueous film-forming solutions, surfactants, emulsion forming additives, a polymer, dimethylsulfoxide, ethyl acetate, acetone, methyl ethyl ketone, a polyethylene glycol ester of an aliphatic acid, methylene chloride, chloroform, and mixtures thereof, and b) an agent selected from the group consisting of a dye, a foliar fertilizer or insecticide. and c) pentacyclic triterpene compound exhibiting a structure of formula II or formula III:

II

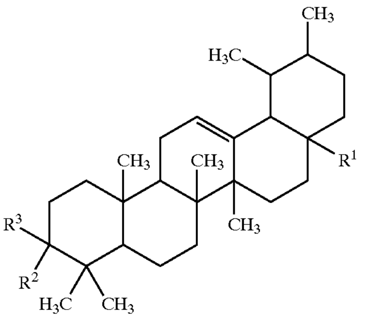

III

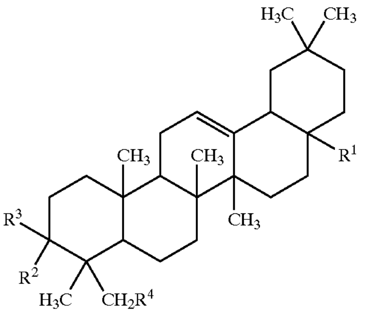

wherein:

$R^1$=$CH_2O$—X—$Y^2$, $CH_2NHY^1$, $CH_2NY^1_2$, $CH_2Y^3$, $CH_2NH$—X—OH, $CH_2NH$—X—$Y^2$, $CH_2NH$—X—$Y^3$, $CH_2NH$—X—$OY^1$, $CH_2O$—X—$OY^1$, $CO_2Y^1$, $COY^3$, $COY^2$, CHO, CH═$N(CH_2)_m(O(CH_2)_m)_nR^4$, or CH═$N(CH_2)_m(O(CH_2)_m)_nY^2$;

$R^2$, $R^3$=H, OH, $OY^1$, O—X—OH, O—X—$OY^1$, O—X—$Y^2$, $Y^3$, $NHY^1$, $NY^1_2$, $Y^3$, NH—X—OH, NH—X—$Y^2$, NH—X—$Y^3$, NH—X—$OY^1$, $NY^1$—X—OH, $NY^1$—X—$Y^2$, $NY^1$—X—$Y^3$, or $NY^1$—X—$OY^1$; provided that one of $R^2$ or $R^3$ is H or that $R^2$ and $R^3$ together denote carbonyl oxygen;

$R^4$=H, OH, $OY^1$, or $Y^3$;

$Y^1$=H, alkyl of 1–30 carbon atoms, straight chain or branched, cycloalkyl of 3–30 carbon atoms, alkanyl of 3–30 carbon atoms, oxyalkyl of 4–30 carbon atoms, phenylalkyl of 7–30 carbon atoms, or phenoxyalkyl of 7–30 carbon atoms;

$Y^2$=$NH_2$, $NHY^1$, or $NY^1_2$;

$Y^3$=—$(O(CH_2)_m)_nR^4$ or —$(O(CH_2)_m)_nY^2$, where m=2–4 and n=1–230;

X=—$OC(CH_2)_pCO$— where p=1–22.

2. A composition according to claim 1 further comprising a foliar fertilizer, or insecticide.

3. A grain grass having external surfaces covered by a composition according to claim 1.

4. A grain grass according to claim 3 selected from the group consisting of rye, wheat, or barley.

5. A method for protecting plants against fungus attack by a process comprising:

applying to exposed plant surfaces a carrier and an effective amount of a composition containing a pentacyclic triterpene compound exhibiting a structure according to formula II or formula III:

II

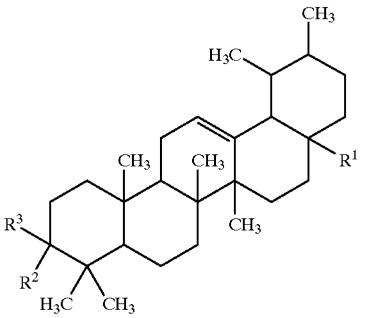

III

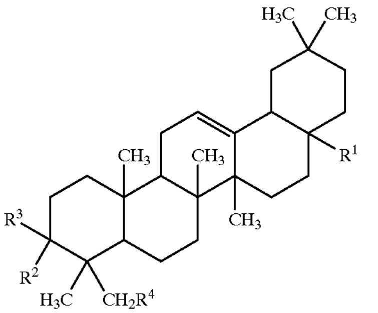

wherein:

$R^1$=$CH_2O$—X—$Y^2$, $CH_2NHY^1$, $CH_2NY^1_2$, $CH_2Y^3$, $CH_2NH$—X—OH, $CH_2NH$—X—$Y^2$, $CH_2NH$—X—$Y^3$, $CH_2NH$—X—$OY^1$, $CH_2OC(O)$—$OY^1$, $CH_2O$—X—$OY^1$, $CO_2Y^1$, $COY^3$, $COY^2$, CHO, CH═N$(CH_2)_m(O(CH_2)_m)_nR^4$, or CH═$N(CH_2)_m(O(CH_2)_m)_nY^2$;

$R^2$, $R^3$=H, OH, $OY^1$, O—X—OH, O—X—$OY^1$, O—X—$Y^2$, $Y^3$, $NHY^1$, $NY^1_2$, $Y^3$, NH—X—OH, NH—X—$Y^2$, NH—X—$Y^3$, NH—X—$OY^1$, $NY^1$—X—OH, $NY^1$—X—$Y^2$, $NY^1$—X—$Y^3$, or $NY^1$—X—$OY^1$; provided that one of $R^2$ or $R^3$ is H or that $R^2$ and $R^3$ together denote carbonyl oxygen;

$R^4$=H, OH, $OY^1$, or $Y^3$;

$Y^1$=H, alkyl of 1–30 carbon atoms, straight chain or branched, cycloalkyl of 3–30 carbon atoms, alkanyl of 3–30 carbon atoms, oxyalkyl of 4–30 carbon atoms, phenylalkyl of 7–30 carbon atoms, or phenoxyalkyl of 7–30 carbon atoms;

$Y^2$=$NH_2$, $NHY^1$, or $NY^1_2$;

$Y^3$=—$(O(CH_2)_m)_nR^4$ where m=2–4 and n=1–230;

X=—$OC(CH_2)_pCO$— where p=1–22.

6. A method as in claim 5 wherein the applying step comprises applying said composition to surfaces of grain grasses.

7. A method as in claim 5 wherein said carrier is selected from the group consisting of an aqueous film-forming solution, a surfactant, an emulsion forming additive, and a polymer.

8. A method as in claim 5 wherein said carrier is selected from the group consisting of aqueous film-forming solutions, dimethylsulfoxide, ethyl acetate, acetone, methyl ethyl ketone, methylene chloride, chloroform, and mixtures thereof.

9. A method as in claim 5 wherein said composition contains a solvent for said pentacyclic triterpene compound.

10. A method as in claim 9 wherein said solvent is selected from ethyl acetate, acetone, methyl ethyl ketone, ethanol, propanol, isopropanol, methanol, methylene chloride, chloroform, or their mixtures.

11. A method according to claim 9 wherein said solvent contains 1–25 wt % acetone, about 0–10 wt % dimethylsulfoxide, 0–35% polyethyleneglycol ester of an aliphatic acid, and about 0–25 wt % of a surfactant.

12. A method as in claim 5 wherein said pentacyclic triterpene compound is applied to said plant surfaces at a rate sufficient to prevent pathogenic infections.

13. A method as in claim 12 wherein said pentacyclic triterpene compound is applied to said plant surfaces at a rate within the range of 0.1–1000 kg/h.

14. A method as in claim 13 wherein said pentacyclic triterpene compound is applied to said plant surfaces at a rate within the range of 0.1–100 kg/h.

15. A composition according to claim 1 containing water and 7–30 grams of the selected pentacyclic triterpene per gallon of water.

16. A composition according to claim 1 wherein said carrier comprises a solvent for pentacyclic triterpenes that comprises 1–25 wt% acetone, 0–10 wt% DMSO, 0–35 wt% of a polyethyleneglycol ester of an aliphatic acid, and 0–25 wt% of a surfactant.

17. A composition according to claim 1 comprising a pentacyclic triterpene that exhibits a structure according to Formula II.

18. A composition according to claim 1 comprising a pentacyclic triterpene that exhibits a structure according to Formula III.

* * * * *